(12) United States Patent
Rey et al.

(10) Patent No.: US 10,662,178 B2
(45) Date of Patent: May 26, 2020

(54) CRYSTALLINE FORM OF OLAPARIB

(71) Applicant: Apotex Inc., Toronto (CA)

(72) Inventors: Allan W. Rey, Brantford (CA); Fabio E. S. Souza, Mississauga (CA); Annyt Bhattacharyya, Hamilton (CA); Bahareh Khalili, Mississauga (CA)

(73) Assignee: Apotex Inc., Toronto, Ontario (CA)

( * ) Notice: Subject to any disclaimer, the term of this patent is extended or adjusted under 35 U.S.C. 154(b) by 0 days.

(21) Appl. No.: 16/261,901

(22) Filed: Jan. 30, 2019

(65) Prior Publication Data

US 2019/0233400 A1 Aug. 1, 2019

Related U.S. Application Data

(60) Provisional application No. 62/624,228, filed on Jan. 31, 2018.

(51) Int. Cl.
| | | |
|---|---|---|
| C07D 403/12 | (2006.01) |
| A61K 9/48 | (2006.01) |
| A61K 9/20 | (2006.01) |
| A61K 31/00 | (2006.01) |
| A61K 31/497 | (2006.01) |

(52) U.S. Cl.
CPC .............. *C07D 403/12* (2013.01); *A61K 9/20* (2013.01); *A61K 9/48* (2013.01); *A61K 31/00* (2013.01); *A61K 31/497* (2013.01); *C07B 2200/13* (2013.01)

(58) Field of Classification Search
CPC .................................................. C07D 403/12
See application file for complete search history.

(56) References Cited

U.S. PATENT DOCUMENTS

| | | | |
|---|---|---|---|
| 8,183,369 B2 | 5/2012 | Quigley et al. |
| 8,247,416 B2 | 8/2012 | Menear et al. |
| 8,475,842 B2 | 7/2013 | Bechtold et al. |
| 2017/0105937 A1 | 4/2017 | Sheikh et al. |
| 2017/0174662 A1 | 6/2017 | Novo et al. |
| 2018/0050991 A1 | 2/2018 | Lin et al. |

FOREIGN PATENT DOCUMENTS

| | | |
|---|---|---|
| CN | 104434809 A | 3/2015 |
| CN | 105061328 A | 11/2015 |
| CN | 105254572 A | 1/2016 |
| CN | 105439961 A | 3/2016 |
| CN | 105503739 A | 4/2016 |
| CN | 105753789 A | 7/2016 |
| CN | 105777651 A | 7/2016 |
| CN | 106554315 A | 4/2017 |
| CN | 106699672 A | 5/2017 |
| CN | 107098862 A | 8/2017 |
| CN | 107162985 A | 9/2017 |
| CN | 107235914 A | 10/2017 |
| CN | 107266370 A | 10/2017 |
| CN | 107304186 A | 10/2017 |
| CN | 107304187 A | 10/2017 |
| CN | 107382873 A | 11/2017 |
| CN | 108101852 A | 6/2018 |
| CN | 108586355 A | 9/2018 |
| EP | 3184513 A1 | 6/2017 |
| EP | 3263095 A1 | 1/2018 |
| WO | 2004080976 A1 | 9/2004 |
| WO | 2008047082 A2 | 4/2008 |
| WO | 2009050469 A1 | 4/2009 |
| WO | 2010041051 A1 | 4/2010 |
| WO | 2017123156 A1 | 7/2017 |
| WO | 2017140283 A1 | 8/2017 |
| WO | 2017153958 A1 | 9/2017 |
| WO | 2017191562 A1 | 11/2017 |

OTHER PUBLICATIONS

"CHMP assessment report for Lynparza (Procedure No. EMEA/H/C/003726/0000)" European Medicines Agency Science Medicines Health, Oct. 23, 2014, pp. 1-187, European Medicines Agency, London, United Kingdom.
Bernstein, "Polymorphism in Molecular Crystals", 2002, pp. 9-10, Oxford University Press, Oxford, United Kingdom.
"Remington: The Science and Practice of Pharmacy", 2006, pp. 889-938, Lippincott Williams & Wilkins, Philadephia, PA.

*Primary Examiner* — Brian E McDowell
(74) *Attorney, Agent, or Firm* — The Webb Law Firm

(57) ABSTRACT

The present invention provides a novel crystalline form of Olaparib comprising Olaparib and benzyl alcohol, compositions thereof, and the use of this crystalline form in the treatment of cancers, such as germline BRCA-mutated (gBRCAm) advanced ovarian cancer.

14 Claims, 1 Drawing Sheet

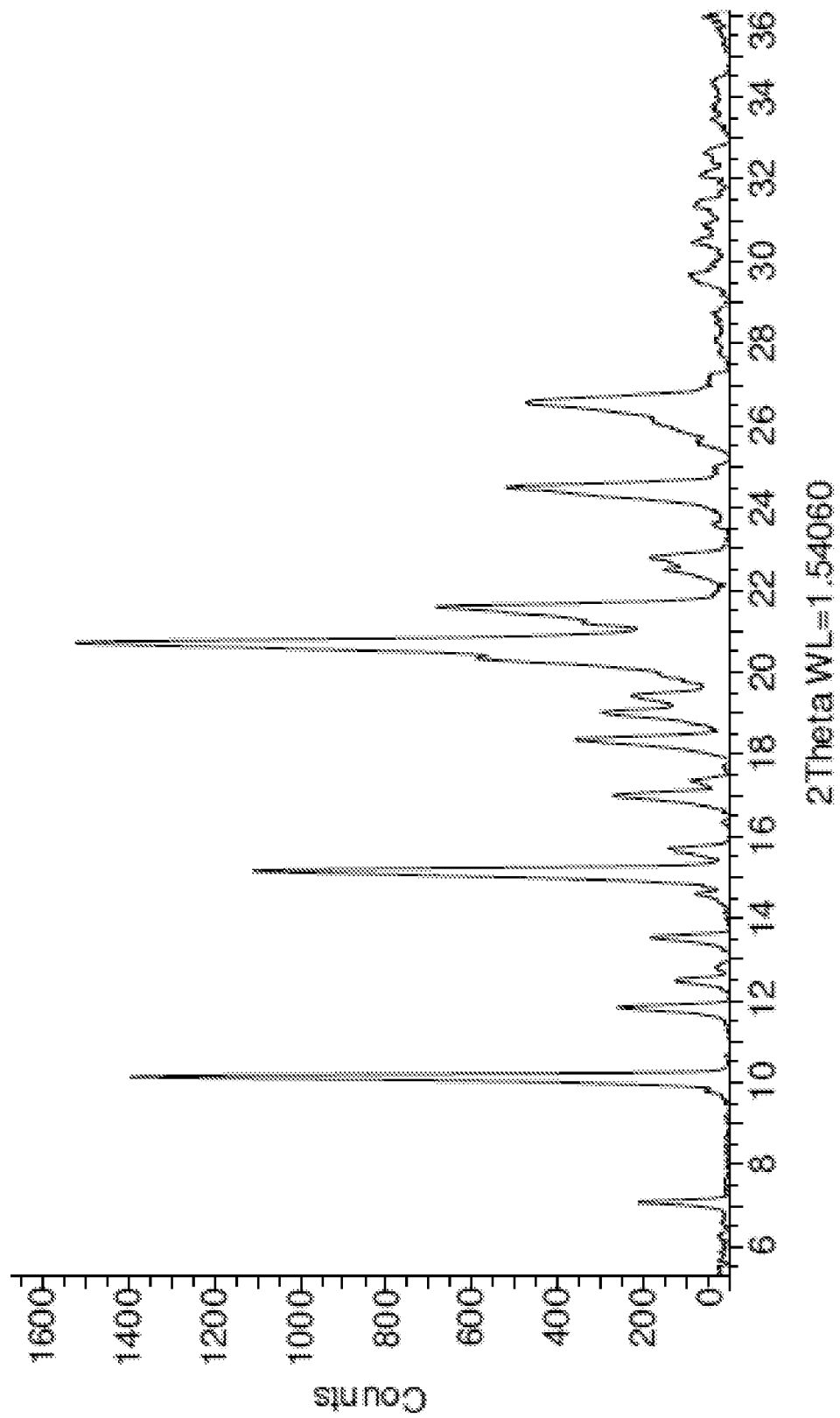

CRYSTALLINE FORM OF OLAPARIB

CROSS-REFERENCE TO RELATED APPLICATION

This application claims the benefit of U.S. Provisional Patent Application No. 62/624,228, filed Jan. 31, 2018, the disclosure of which is hereby incorporated by reference in its entirety.

TECHNICAL FIELD

The present invention is directed to novel crystalline forms of Olaparib, pharmaceutical compositions containing these forms, and their use to treat cancer.

BACKGROUND

The compound 4-[(3-{[4-(cyclopropylcarbonyl)-piperazin-1-yl]carbonyl}-4-fluorophenyl)methyl]phthalazin-1(2H)-one, commonly known as Olaparib, is described in WO 2004/080976 A1. Olaparib, which is marketed in the United States as LYNPARZA®, is an inhibitor of the enzyme poly ADP ribose polymerase (PARP), and is indicated for the treatment of adult patients with deleterious or suspected deleterious germline BRCA-mutated (gBRCAm) advanced ovarian cancer who have been treated with three or more prior lines of chemotherapy.

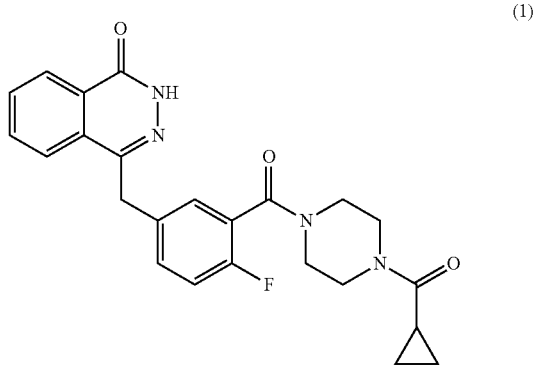 [SMILES: O=C(c1cc(Cc2n[nH]c(=O)c3ccccc23)ccc1F)N1CCN(C(=O)C2CC2)CC1]

(1)

Crystalline forms of Olaparib, including solvated and hydrated forms, are known, and have been disclosed, for example, in WO 2008/047082 A2, WO 2009/050469 A1, WO 2010/041051 A1, WO 2017/123156 A1, and WO 2017/140283 A1.

According to the European CHMP Assessment Report for LYNPARZA® (EMEA/H/C/003726/0000), the drug substance Olaparib in the approved drug product has both low solubility and low permeability, placing Olaparib in Class IV of the Biopharmaceutics Classification System (BCS). Of the four BCS Classes, owing to their low solubility and poor permeability, Class IV drug substances present the most challenges to achieving adequate bioavailability.

Approaches to improving the solubility of a drug substance include, for example, particle size reduction techniques, dispersion of the drug substance onto an inert carrier, and formulation of the drug substance together with solubilizing excipients. According to the CHMP report for LYNPARZA®, the drug substance Olaparib in the originally approved capsule form of LYNPARZA®, is micronized and formulated as a crystalline solid dispersion in lauroyl macrogol-32 glycerides (LMG) to optimize solubility and bioavailability. However, in order to maintain an optimal ratio of active substance to LMG, the percentage of Olaparib in each dosage of the drug product is very low, requiring a dosage regimen of 16 capsules having 50 mg strength daily to provide adequate plasma levels. Subsequent 100 mg and 150 mg tablet forms of Olaparib have since been approved in the United States that provide improved bioavailability and allow for a daily dose reduction from 800 mg to 600 mg that is also deliverable in fewer dose units. The development of 100 mg and 150 mg tablet forms of Olaparib is described in WO 2010/041051 A1, wherein the drug substance is present in an amorphous form as a dispersion with a matrix polymer such as copovidone. However, amorphous forms tend to have lower stability compared to crystalline forms, and methods for their preparation can be complex on an industrial scale. As a result, there remains a need for new crystalline forms of Olaparib providing a suitable dissolution profile without requiring micronization or the preparation of an amorphous form.

Different crystalline forms of the same compound may have different crystal packing, thermodynamic, spectroscopic, kinetic, surface and mechanical properties. For example, different crystalline forms may have different stability properties such that a particular crystalline form may be less sensitive to heat, relative humidity (RH) and/or light. Alternatively or additionally, a particular crystalline form may provide more favourable compressibility and/or density properties, thereby providing more desirable characteristics for formulation and/or product manufacturing. Differences in stability between solid forms of a drug may result from changes in chemical reactivity, such as differential oxidation. Such properties may provide for more suitable product qualities, including a dosage form that is more resistant to discolouration when comprised of a specific crystalline form. Particular crystalline forms may also have different solubilities, thereby providing different pharmacokinetic parameters, which allow for specific crystalline forms to be used in order to achieve specific pharmacokinetic targets. Differences in solubility between crystalline forms are particularly relevant for compounds exhibiting low aqueous solubility, such as BCS Class IV drug substances such that even a modest increase in solubility may provide a beneficial enhancement in bioavailability.

Although general approaches to crystalline form screening of active pharmaceutical ingredients are known, it is well established that the prediction of whether any given compound will exhibit polymorphism is not possible. For example, in the case of Olaparib, different crystalline forms can arise even when using the same preparation solvent or solvent mixture. As reported in WO 2009/050469 A1 and WO 2008/047082 A2, ethanol/water mixtures and methanol/water mixtures afford either Form A or Form L, which are both anhydrous forms. Furthermore, the use of water as the sole solvent can result in formation of hydrate, such as Form H as reported in WO 2010/041051 A1. Further examples of this dichotomy are reported with acetonitrile and acetic acid/water mixtures. Accordingly, it is not possible to extend generalities to the number and kinds of crystalline forms that can exist for Olaparib, or to what methods will be suitable for the preparation of any given crystalline form. Furthermore, prediction of the properties of any unknown crystalline forms, and how they will differ from other crystalline forms of the same compound, remains elusive (Joel Bernstein, *Polymorphism in Molecular Crystals*, Oxford University Press, New York, 2002, page 9).

Due to the classification of Olaparib as a BCS Class IV drug substance, and the prior need to provide Olaparib in a micronized form or as an amorphous material in order to provide suitable bioavailability, there exists a need for novel crystalline forms of Olaparib for use in providing drug products containing Olaparib and their manufacture.

SUMMARY

The Olaparib crystalline form of the present invention comprises Olaparib that has crystallized with benzyl alcohol in the same crystal lattice. Benzyl alcohol has an established safety record, and can therefore safely be used in materials intended for use in the preparation of pharmaceutical compositions for administration to humans or animals. Further, benzyl alcohol has been known to act as a solubilizer for some compounds. Thus, the provision of a crystalline form of Olaparib comprising benzyl alcohol in the same crystal lattice is expected to provide improvements in the solubility of Olaparib without requiring micronization of the crystalline form, the conversion of this crystalline form to an amorphous form, or the preparation of a dispersion.

The present invention provides a crystalline form of Olaparib that can be prepared by an efficient and industrially compatible process. Surprisingly, although the solvent system used incorporates three components at the time of initial crystallization, only one, benzyl alcohol, is substantially retained within the crystal lattice. The other two components, methyl t-butyl ether and heptanes, are controlled to levels below the limits established by the ICH (International Council for Harmonisation of Technical Requirements for Pharmaceuticals for Human Use). In contrast to other crystalline forms of Olaparib where water is known to be capable of displacing solvated solvents such as ethanol, the crystalline form of the present invention exhibits stability when exposed to conditions of 40° C./75% RH.

Accordingly, in a first aspect of the present invention, there is provided a crystalline form of Olaparib comprising benzyl alcohol and Olaparib. Preferably, in the crystalline form of the first aspect, the molar ratio of Olaparib to benzyl alcohol is between approximately 1:0.25 and approximately 1:1.25. More preferably, the molar ratio of Olaparib to benzyl alcohol is between approximately 1:0.25 and approximately 1:0.75. Most preferably, the molar ratio of Olaparib to benzyl alcohol in the crystalline form of the first aspect is between approximately 1:0.4 and approximately 1:0.6.

In a second aspect of the present invention, there is provided a crystalline form of Olaparib, Olaparib Form APO-I, comprising Olaparib and benzyl alcohol that is characterized by a PXRD diffractogram comprising peaks, expressed in degrees 2θ (±0.2°), at 10.1°, 12.5° and 20.7°. In a preferred embodiment of the second aspect, the PXRD diffractogram further comprises at least three peaks, expressed in degrees 2θ (±0.2°), selected from the group consisting of: 7.1°, 11.8°, 13.5°, 15.2°, 17.0°, 18.4°, 19.0°, 21.6°, 24.5° and 26.6°. In a more preferred embodiment of the second aspect, the PXRD diffractogram further comprises peaks, expressed in degrees 2θ (±0.2°), at 7.1°, 11.8°, 13.5°, 15.2°, 17.0°, 18.4°, 19.0°, 21.6°, 24.5° and 26.6°. Preferably, the crystalline form of the second aspect of the invention provides a PXRD diffractogram comprising peaks in substantially the same positions (±0.2° 2θ) as those shown in FIG. 1. In a further preferred embodiment of the second aspect, the molar ratio of Olaparib to benzyl alcohol in the crystalline form is between approximately 1:25 and approximately 1:0.75.

In a third aspect of the present invention, there is provided a process for the preparation of a crystalline form of Olaparib according to the first or second aspects of the invention, the process comprising:
 (1) Dissolving Olaparib in benzyl alcohol at a suitable temperature to provide a solution;
 (2) Adding an anti-solvent to the solution to provide a mixture;
 (3) Cooling the mixture, if necessary, to form a suspension comprising the crystalline form; and
 (4) Isolating the crystalline form from the suspension.

Preferably, in the third aspect of the present invention, there is provided a process for the preparation of a crystalline form of Olaparib according to the second aspect of the invention.

In a preferred embodiment of the third aspect, adding an anti-solvent comprises adding a first anti-solvent, which is a hydrocarbon having 5 to 7 carbon atoms, and a second anti-solvent, which is an ether having 4 or 5 carbon atoms. Preferably, the first anti-solvent is heptanes and the second anti-solvent is methyl t-butyl ether. In another preferred embodiment of the third aspect of the invention, the suitable temperature is between approximately 45° C. and approximately 60° C. In another preferred embodiment of the third aspect, the molar ratio of Olaparib to benzyl alcohol in the crystalline form prepared is between approximately 1:0.25 and approximately 1:0.75. Most preferably, the molar ratio of Olaparib to benzyl alcohol in the crystalline form is between approximately 1:0.4 and approximately 1:0.6.

In a fourth aspect of the present invention, there is provided a pharmaceutical composition comprising a crystalline form of Olaparib according to the first or second aspects of the invention, and one or more pharmaceutically acceptable excipients. Preferably, the pharmaceutical composition is in the form of a solid dosage form. Most preferably, the pharmaceutical composition is a capsule or tablet. Preferably, the pharmaceutical composition of the fourth aspect comprises an amount of the crystalline form of Olaparib of the first or second aspects that is equivalent to 50 mg, 100 mg or 150 mg Olaparib.

In a fifth aspect of the present invention, there is provided a use of a crystalline form of Olaparib according to the first or second aspects of the invention, or the pharmaceutical composition of the fourth aspect of the invention, in the treatment of cancer. In a preferred embodiment of the fifth aspect, the cancer is germline BRCA-mutated (gBRCAm) advanced ovarian cancer.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention are described, by way of example only, with reference to the attached FIGURE.

FIG. 1 is a representative PXRD diffractogram of Olaparib Form APO-I as prepared in Example 1.

DETAILED DESCRIPTION

The Olaparib crystalline form of the present invention comprises Olaparib that has crystallized with benzyl alcohol in the same crystal lattice. Importantly, with respect to the use of this crystalline form in the preparation of pharmaceutical compositions for use in the treatment of cancer, benzyl alcohol is included in both the U.S. Food & Drug Administration's (FDA's) Everything Added to Food in the United States (EAFUS) list, and the Inactive Ingredient Database (IID). The EAFUS list contains ingredients added directly to food that the FDA has either approved as food additives, or has listed or affirmed as being GRAS (Generally Recognized As Safe). The IID list provides information on inactive ingredients present in FDA-approved drug products. Once an inactive ingredient has appeared in an approved drug product for a particular route of administration, the inactive ingredient is not considered new and may require a less extensive review the next time it is included in a new drug product. Also of importance to the present invention is that benzyl alcohol is known to act as a solubilizer for some compounds. Thus, the provision of a crystalline form of Olaparib comprising Olaparib and benzyl alcohol in the same crystal lattice is expected to provide improvements in the solubility of Olaparib without requiring micronization of the crystalline form or its conversion to an amorphous form.

The Olaparib crystalline form of the present invention exhibits differences in properties when compared to the known crystalline forms of Olaparib. Properties that differ between the invention and known crystalline forms of Olaparib include crystal packing properties such as molar volume, density and hygroscopicity; thermodynamic properties such as melting point and solubility; kinetic properties such as dissolution rate and chemical/polymorphic stability; surface properties such as crystal habit/particle morphology; and/or mechanical properties such as hardness, tensile strength, compactibility, tableting, handling, flow, and blending.

Furthermore, the Olaparib crystalline form of the present invention exhibits stability under conditions of high temperature and high humidity. As reported in WO 2008/047082 A2, water is capable of displacing solvated solvents such as ethanol from the crystal structure of solvated forms of Olaparib. Accordingly, there is a risk that water vapour present in humid atmospheric conditions could also result in such displacement for other multi-component crystalline forms of Olaparib. This is a problem that was observed during the development of the present invention, where several of the initially prepared Olaparib crystalline forms (crystalline forms containing acetic acid, 2-butanol and acetophenone within the crystalline lattice) showed this tendency towards desolvation by atmospheric moisture. In contrast, the crystalline form of the present invention, wherein benzyl alcohol has crystallized with Olaparib in the crystalline lattice, was unchanged following exposure to conditions of 40° C./75% RH for at least 20 days.

Further, the present invention provides a crystalline form of Olaparib that can be prepared by an efficient and industrially compatible process. Surprisingly, the crystalline form of the present invention, wherein benzyl alcohol has crystallized with Olaparib in the same crystalline lattice, can be prepared from a solvent mixture comprised of three different components: benzyl alcohol, heptanes, and methyl t-butyl ether. Despite the use of a three-component system, only benzyl alcohol is substantially retained within the crystal lattice of the crystalline form of the invention. Importantly, the other two components of the solvent mixture, methyl t-butyl ether and heptanes, are controlled to levels below established ICH guidelines.

Depending on the manner in which the crystalline forms of the present invention are prepared, and the methodology and instrument used for PXRD analysis, the intensity of a given peak observed in a PXRD diffractogram of the crystalline form may vary when compared to the same peak in the representative PXRD diffractogram provided in FIG. 1. Thus, differences in relative peak intensities between peaks in a PXRD diffractogram for a given crystalline form may be observed when compared to the relative peak intensities of the peaks in the representative PXRD diffractogram of FIG. 1. Any such differences may be due, in part, to the preferred orientation of the sample and its deviation from the ideal random sample orientation, the preparation of the sample for analysis, and the methodology applied for the analysis. Such variations are known and understood by a person of skill in the art, and any such variations do not depart from the invention disclosed herein.

In addition to the differences in relative peak intensities that may be observed in comparison to the representative PXRD diffractogram provided in FIG. 1, it is understood that individual peak positions may vary between ±0.2° 2θ from the values observed in the representative PXRD diffractogram provided in FIG. 1 for the crystalline form of the invention, or listed in Table 1. Such variations are known and understood by a person of skill in the art, and any such variations do not depart from the invention disclosed herein.

Further, depending on the instrument used for X-ray analysis and its calibration, uniform offsets in the peak position of each peak in a PXRD diffractogram of greater that 0.2° 2θ may be observed when compared to the representative PXRD diffractogram provided in FIG. 1. Thus, PXRD diffractograms of the crystalline form of the present invention may, in some circumstances, display the same relative peak positions as observed in the representative PXRD diffractogram provided in FIG. 1, with the exception that each peak is offset in the same direction, and by approximately the same amount, such that the overall PXRD diffractogram is substantially the same in appearance as the PXRD diffractogram of FIG. 1, with the exception of the uniform offset in peak positions. The observation of any such uniform peak shift in a PXRD diffractogram does not depart from the invention disclosed herein given that the relative peak positions of the individual peaks within the PXRD diffractogram remain consistent with the relative peak positions observed in the PXRD diffractogram of FIG. 1.

As used herein, the term 'crystalline form' refers to a substance with a particular arrangement of molecular components in its crystal lattice, and which may be identified by physical characterization methods such as PXRD. As used herein, the term crystalline form is intended to include single-component and multiple-component crystalline forms. Single-component forms of Olaparib, such as those known in the art, consist solely of Olaparib in the repeating unit of the crystal lattice. Multiple-component forms of Olaparib, such as the present invention, include crystalline forms of Olaparib wherein one or more other molecules are also incorporated into the crystal lattice with Olaparib.

Multi-component crystalline forms comprising more than one type of molecule may have some variability in the exact molar ratio of their components depending on the conditions used for their preparation. For example, a molar ratio of components within a multi-component crystalline form provides a person of skill in the art information as to the general relative quantities of the components of the crystalline form. In many cases, the molar ratio may vary by ±20% from a stated range. With respect to the present invention, a molar ratio of 1:0.4 should be understood to include the ratios 1:0.3 and 1:0.5, as well as all of the individual ratios in between.

As used herein, the term "room temperature" refers to a temperature in the range of 20° C. to 25° C.

When describing the embodiments of the present invention there may be a common variance to a given temperature or time that would be understood or expected by the person skilled in the art to provide substantially the same result. For example, when reference is made to a particular temperature, it is to be understood by the person skilled in the art that there is an allowable variance of ±5° C. associated with that temperature. When reference is made to a particular time, it is to be understood that there is an allowable variance of ±10 minutes when the time is one or two hours, and ±1 hour when longer periods of time are referenced.

In one embodiment of the present invention, there is provided a new crystalline form of Olaparib, Olaparib Form APO-I, comprising Olaparib and benzyl alcohol. Preferably, in Olaparib Form APO-I, the molar ratio of Olaparib to benzyl alcohol is between approximately 1:0.4 and approximately 1:0.6.

Olaparib Form APO-I can be characterized by a PXRD diffractogram comprising, among other peaks, characteristic peaks, expressed in degrees 2θ (±0.2°), at 10.1°, 12.5° and 20.7°. Preferably, the PXRD diffractogram further comprises at least three peaks, expressed in degrees 2θ (±0.2°), selected from the group consisting of 7.1°, 11.8°, 13.5°, 15.2°, 17.0°, 18.4°, 19.0°, 21.6°, 24.5° and 26.6°. More preferably, the PXRD diffractogram further comprises peaks, expressed in degrees 2θ (±0.2°), 7.1°, 11.8°, 13.5°, 15.2°, 17.0°, 18.4°, 19.0°, 21.6°, 24.5° and 26.6°. PXRD studies of capped and uncapped samples of Olaparib Form APO-I maintained in a 40° C./75% RH stability chamber for at least 20 days showed that no change in the crystalline form occurred.

An illustrative PXRD diffractogram of Olaparib Form APO-I, as prepared in Example 1, is shown in FIG. 1. A peak listing, comprising representative peaks from the PXRD diffractogram in FIG. 1, and their relative intensities, is provided in Table 1. Although illustrative of the PXRD diffractogram that is provided for the Olaparib Form APO-I of the present invention, the relative intensities of the peaks are variable. Thus, depending on a particular sample, the prominence or relative intensity of the peaks observed may differ from those in the illustrative PXRD diffractogram and peak listing.

TABLE 1

Relative peak intensities of Olaparib Form APO-I from FIG. 1

| Angle (2θ) | Relative intensity (%) |
|---|---|
| 7.08 | 13.9 |
| 10.14 | 91.5 |
| 11.84 | 16.9 |
| 12.49 | 8.1 |
| 13.53 | 11.9 |
| 15.15 | 72.6 |
| 15.69 | 9.1 |
| 16.99 | 17.8 |
| 18.36 | 23.6 |
| 19.01 | 19.5 |
| 20.71 | 100.00 |
| 21.58 | 44.8 |
| 24.49 | 34.1 |
| 26.56 | 31.1 |

As described in Example 1, Olaparib Form APO-1 can be prepared by dissolving Olaparib in a minimal amount of benzyl alcohol, preferably at a temperature of between approximately 45° C. and approximately 60° C., to provide a solution; adding an anti-solvent; maintaining the mixture at a suitable temperature, which is preferably an elevated temperature; allowing the mixture to cool to afford a suspension comprising Olaparib Form APO-I. Preferably, the cooled mixture is maintained at room temperature or below to facilitate crystallization.

The anti-solvent used is preferably a mixture of a first anti-solvent and second anti-solvent. The first anti-solvent is preferably a saturated hydrocarbon having 5 to 7 carbon atoms, and is more preferably a saturated hydrocarbon selected from the group consisting of pentane, hexane, cyclohexane, heptane and isomeric mixtures thereof such as hexanes and heptanes. The second anti-solvent is preferably an ether having 4 or 5 carbon atoms such as tetrahydrofuran or methyl t-butyl ether. Preferably, the second anti-solvent aids miscibility between the benzyl alcohol and the first anti-solvent.

Isolation of the crystalline form from the suspension, preferably by filtration, and optional drying of the filtered material, preferably in vacuo and/or at elevated temperature, provides Olaparib Form APO-I having a PXRD diffractogram consistent with FIG. 1.

In a further embodiment of the invention, there is provided a pharmaceutical composition of a crystalline form of Olaparib comprising Olaparib and benzyl alcohol, with one or more pharmaceutically acceptable excipients. Preferably, the pharmaceutical composition is a solid dosage form suitable for oral administration, such as a capsule, tablet, pill, powder, or granulate. Most preferably, the pharmaceutical composition is a capsule or tablet. Preferably, the pharmaceutical composition provides a dose of Olaparib that is equivalent to the 50 mg, 100 mg or 150 mg of Olaparib found in LYNPARZA® drug products.

Suitable pharmaceutically acceptable excipients are preferably inert with respect to the crystalline form of Olaparib of the present invention, and may include, for example, one or more excipients selected from binders such as lactose, starches, modified starches, sugars, gum acacia, gum tragacanth, guar gum, pectin, wax binders, microcrystalline cellulose, methylcellulose, carboxymethylcellulose, hydroxypropyl methylcellulose, hydroxyethyl cellulose, hydroxypropyl cellulose, copolyvidone, gelatine, polyvinylpyrrolidone (PVP) and sodium alginate; fillers or diluents such as lactose, sugar, starches, modified starches, mannitol, sorbitol, inorganic salts, cellulose derivatives (e.g., microcrystalline cellulose, cellulose), calcium sulphate, xylitol and lactitol; disintegrants such as croscarmellose sodium, crospovidone, polyvinylpyrrolidone, sodium starch glycollate, corn starch, microcrystalline cellulose, hydroxypropyl methylcellulose and hydroxypropyl cellulose; lubricants such as magnesium stearate, magnesium lauryl stearate, sodium stearyl fumarate, stearic acid, calcium stearate, zinc stearate, potassium benzoate, sodium benzoate, myristic acid, palmitic acid, mineral oil, hydrogenated castor oil, medium-chain triglycerides, poloxamer, polyethylene glycol and talc; and dispersants or solubility enhancing agents, such cyclodextrins, glyceryl monostearate, hypromellose, meglumine, Poloxamer, polyoxyethylene castor oil derivatives, polyoxyethylene stearates, polyoxylglycerides, povidone, and stearic acid. Other excipients including preservatives, stabilisers, anti-oxidants, silica flow conditioners, antiadherents or glidants may be added as required. Other suitable excipients and the preparation of solid oral dosage forms is well known to person of skill in the art, and is described generally, for example, in *Remington The Science*

*and Practice of Pharmacy* 21*st* Edition (Lippincott Williams & Wilkins: Philadelphia; 2006; Chapter 45).

Optionally, when the pharmaceutical compositions are solid dosage forms, the solid dosage forms may be prepared with coatings, such as enteric coatings and extended release coatings, using standard pharmaceutical coatings. Such coatings, and their application, are well known to persons skilled in the art, and are described, for example, in *Remington The Science and Practice of Pharmacy* 21*st* Edition (Lippincott Williams & Wilkins: Philadelphia; 2006; Chapter 46).

EXAMPLES

The following non-limiting example is illustrative of some of the aspects and embodiments of the invention described herein.

The Olaparib used as a starting material in the following example was consistent with Olaparib Form A, which is reported in WO 2008/047082 A2. However, other polymorphic forms are equally suitable as starting material, provided complete dissolution of the form occurs when preparing the novel crystalline form of Olaparib of the present invention.

PXRD Analysis:

PXRD diffractograms were recorded on a Bruker D8 Discover powder X-ray diffractometer (Bruker-AXS, Karlsruhe, Germany). The generator was a Micro-focus X-ray source (IMSTube: Cu tube with 1.54060 Å) with a voltage of 50 kV and current of 1.00 mA, using a divergence slit of 0.3 mm and collimator of 0.3 mm. For each sample, one frame was collected using a still scan with a Pilatus 3R-100 kA detector at the distance of 154.72 mm from the sample. Raw data were evaluated using the program EVA (Bruker-AXS, Karlsruhe, Germany).

Example 1: Preparation of Olaparib Form APO-I

Olaparib (100 mg) was suspended in benzyl alcohol (0.4 mL) and heated to 50° C. Complete dissolution of the Olaparib occurred within 10 minutes at this temperature to afford a yellow solution. Heptanes (1.5 mL) was added to provide a biphasic mixture, which changed to a white suspension following addition of methyl t-butyl ether (1.2 mL). The suspension was stirred at 50° C. for 2 hours, then at ambient temperature for 16 hours. After this time, the solid present was collected by filtration, washed with a 1:1 mixture of heptanes:methyl t-butyl ether (2×1 mL) and heptanes (1.5 mL), and dried under ambient conditions for approximately 1.5 hours to afford Olaparib Form APO-I. The PXRD diffractogram of a sample prepared by this method is shown in FIG. 1. $^1$H NMR analysis of the Olaparib Form APO-I (DMSO-$d_6$, 300 MHz) indicated a molar ratio of Olaparib:benzyl alcohol of approximately 1:0.46, negligible heptanes and 2800 ppm methyl t-butyl ether. General yields for the preparation of Olaparib Form APO-I using this method are in the range 80-90%, and the molar ratio of Olaparib:benzyl alcohol is typically in the range of 1:0.4 to 1:0.5.

What is claimed is:

1. A crystalline form of Olaparib comprising Olaparib and benzyl alcohol.

2. The crystalline form of claim 1, wherein the molar ratio of Olaparib to benzyl alcohol is between approximately 1:0.25 and approximately 1:1.25.

3. The crystalline form of claim 1, wherein the molar ratio of Olaparib to benzyl alcohol is between approximately 1:0.25 and approximately 1:0.75.

4. The crystalline form of claim 1, wherein the molar ratio of Olaparib to benzyl alcohol is between approximately 1:0.4 and approximately 1:0.6.

5. The crystalline form of claim 1, characterized by a PXRD diffractogram comprising peaks, expressed in degrees 2θ (±0.2°), at 10.1°, 12.5° and 20.7°.

6. The crystalline form of claim 5, wherein the PXRD diffractogram further comprises at least three peaks, expressed in degrees 2θ (±0.2°), selected from the group consisting of: 7.1°, 11.8°, 13.5°, 15.2°, 17.0°, 18.4°, 19.0°, 21.6°, 24.5° and 26.6°.

7. The crystalline form of claim 5, wherein the PXRD diffractogram further comprises peaks, expressed in degrees 2θ (±0.2°), at 7.1°, 11.8°, 13.5°, 15.2°, 17.0°, 18.4°, 19.0°, 21.6°, 24.5° and 26.6°.

8. The crystalline form of claim 7, providing a PXRD diffractogram comprising peaks in substantially the same positions (±0.2° 2θ) as those shown in FIG. 1.

9. The crystalline form of claim 5, wherein the molar ratio of Olaparib to benzyl alcohol is between approximately 1:0.25 and approximately 1:0.75.

10. The crystalline form of claim 6, wherein the molar ratio of Olaparib to benzyl alcohol is between approximately 1:0.25 and approximately 1:0.75.

11. A pharmaceutical composition comprising the crystalline form of Olaparib of claim 5, and one or more pharmaceutically acceptable excipients.

12. The pharmaceutical composition of claim 11, wherein the pharmaceutical composition is a capsule.

13. The pharmaceutical composition of claim 11, wherein the pharmaceutical composition is a tablet.

14. The pharmaceutical composition of claim 13, wherein the pharmaceutical composition comprises an amount of the crystalline form of Olaparib equivalent to 100 mg or 150 mg Olaparib.

* * * * *

UNITED STATES PATENT AND TRADEMARK OFFICE
CERTIFICATE OF CORRECTION

Page 1 of 1

PATENT NO. : 10,662,178 B2
APPLICATION NO. : 16/261901
DATED : May 26, 2020
INVENTOR(S) : Allan W. Rey et al.

It is certified that error appears in the above-identified patent and that said Letters Patent is hereby corrected as shown below:

In the Specification

Column 3, Line 66, delete "crystalline form is between approximately 1:25 and approxi-" and insert -- crystalline form is between approximately 1:0.25 and approxi- --

Signed and Sealed this
Fourth Day of August, 2020

Andrei Iancu
*Director of the United States Patent and Trademark Office*